United States Patent [19]
Crowninshield

[11] Patent Number: 4,756,307
[45] Date of Patent: Jul. 12, 1988

[54] NAIL DEVICE

[75] Inventor: Roy D. Crowninshield, Warsaw, Ind.

[73] Assignee: Zimmer, Inc., Warsaw, Ind.

[21] Appl. No.: 12,477

[22] Filed: Feb. 9, 1987

[51] Int. Cl.[4] .............................................. A61F 5/04
[52] U.S. Cl. .......................... 128/92 YZ; 128/92 W; 128/92 YR
[58] Field of Search .......... 128/92 YZ, 92 Y, 92 YR, 128/92 W

[56] References Cited

U.S. PATENT DOCUMENTS

| | | | |
|---|---|---|---|
| 4,263,185 | 4/1981 | Belykh et al. | 128/92 YZ |
| 4,338,926 | 7/1982 | Kummer et al. | 128/92 YZ |
| 4,457,301 | 7/1984 | Walker | 128/92 |
| 4,467,793 | 8/1984 | Ender | 128/92 |
| 4,550,723 | 11/1985 | Belykh et al. | 128/92 YZ |
| 4,612,923 | 9/1986 | Kronenthal | 128/92 YR |

FOREIGN PATENT DOCUMENTS 0146398  6/1985  European Pat. Off. ....... 128/92 YR

OTHER PUBLICATIONS

Parsons et al., "Development of a Variable Stiffness, Absorbable Bone Plate", 25th Annual ORS, San Francisco, CA, Feb. 20-22, 1979.

Primary Examiner—Robert A. Hafer
Assistant Examiner—K. G. Rooney
Attorney, Agent, or Firm—Paul D. Schoenle

[57] ABSTRACT

A nail device includes a plurality of segments fastened together by a resorbable bioadhesive such that the plurality of segments are gradually disassociated after the nail device is implanted into a bone. The disassociated segments exhibit less bending and torsional strength and stiffness than the fastened plurality of segments to reduce stress shielding for the bone.

12 Claims, 1 Drawing Sheet

NAIL DEVICE

The present invention relates to a nail device which is to be implanted into a fractured bone to assist in the healing of the fracture.

Heretofore, nail devices in the form of intramedullary rods have been used in fracture fixation. The intramedullary rod provided fracture site alignment, bending stability, and torsional stability. Solid, tubular or open section metal intramedullary tubular or open section rods have been used in this application. The high degree of fracture stability in the presence of limb loading was, and remains, important while the fracture is healing. However, in the presence of a healed fracture, the mechanical strength of the intramedullary rod is no longer needed; and, in many cases the bending and torsional stiffness of the intramedullary rod is not desired to avoid stress shielding. The problem of stress shielding can occur when the intramedullary rod insulates the surrounding bone from normal loading. Consequently, it has been the practice to remove the intramedullary rod after the fracture is healed.

It has been suggested that intramedullary rods can be made from resorbable materials so that over time the intramedullary rod will be absorbed to eliminate the problem of stress shielding. However, the high strength requirement for an intramedullary rod is difficult to achieve in a totally resorbable material or composite. In addition, many nail devices are hammered or otherwise forced into a fractured bone and composite devices are not designed to withstand repeated compressive blows from a hammer or similar tool.

The present invention accommodates the requirements for alignment and stability while also reducing the risk of stress shielding as the fracture is healed. To this end, a nail device comprises a plurality of segments which are initially held together by a resorbable adhesive. When the nail device is initially implanted into a fractured bone, the plurality of segments act as a single solid element providing high strength for alignment, bending stability and rotational stability. However, the absorbable adhesive gradually migrates into the surrounding bone so that the plurality of segments are free to move with respect to each other and shift loading to the surrounding bone.

It is an object of the present invention to retain the benefits of a rigid rod with high strength while also accommodating the problems of stress shielding as the fracture is healing.

Figure 1:
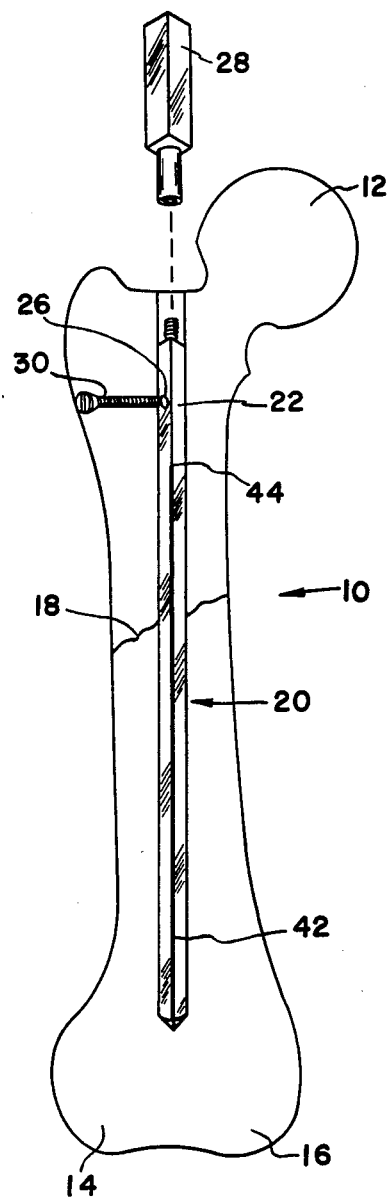
FIG. 1 is a longitudinal view of a femur with a nail device, constructed in accordance with the present invention, implanted to assist in the healing of a fracture.

A femur 10 includes a head 12 in the shape of a ball at a proximal end for cooperation with an acetabular (not shown) and a pair of condyles 14 and 16 at the distal end for cooperation with a knee joint (not shown). The femur 10 is illustrated with a fracture 18 shown at an intermediate location between the proximal and distal ends. In order to assist in the healing of the fracture, a nail device 20 in the form of an intramedullary rod is implanted into the femur to extend across the fracture site.

Figure 2:
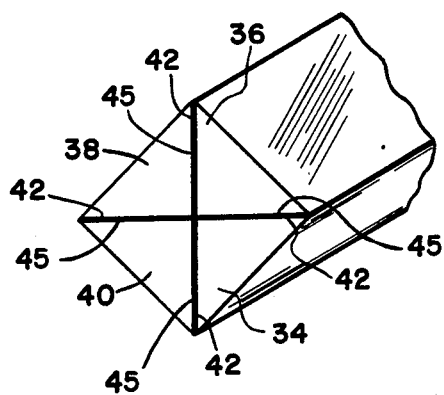
FIG. 2 is a perspective view of the nail device depicted in FIG. 1.

The nail device 20 includes a proximal end 22 with a threaded extension and an aperture 26. The threaded extension is adapted to couple with an impact punch illustrated at 28 so that a hammer or the like can be used to impact the punch as the nail device is driven into the femur. The aperture 26 is optionally provided to receive a bone screw 30 to further secure the nail device 20 to the femur 10. At the proximal end 22 the nail device comprises a solid member while at the distal end 32 the nail device comprises a plurality of segments 34–40 shown in FIG. 2. The plurality of segments are separated from each other by slots or spaces 42 which extend from the distal end to a junction 44. The junction 44 is located near the proximal end so that the slots extend over a substantial length of the nail device 20.

Figure 3:
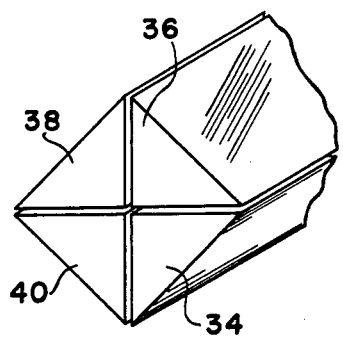
FIG. 3 is a view similar to FIG. 2 after the nail device has been implanted for a sufficient time to heal the fracture.

Before the nail device is implanted into the femur, the slots 42 are filled with a resorbable bioadhesive 45 such as polylactic acid, polyglycolic acid, copolymers or blends of these two, or a protein base adhesive. With the resorbable bioadhesive disposed in the slots, the plurality of segments 34–40 are fastened together to present a solid rod. As such, the solid rod exhibits high strength characteristics which are resistant to bending and rotation. After the nail device 20 is implanted into the femur 10, the resorbable bioadhesive 45 is exposed to the biological environment and resorption occurs, albeit at a gradual rate of absorption. With the bioadhesive resorbed, the plurality of segments will freely disassociate to restricted bone bending and torsion to a lesser extent than previously restricted with the solid rod. Although the plurality of segments 34–40 as shown in FIG. 3 remain adjacent each other in the absence of the resorbable bioadhesive, the cumulative bending stiffness for each individual segment is substantially lower than for the fastened plurality of segments as an individual rod. For example, with the square or diamond cross-section illustrated in FIGS. 2 and 3, the combined bending stiffness of the individual triangular segments is approximately 8% of the bending stiffness of a solid composed of the fastened segments. Therefore, a 92% decrease in bending stiffness is possible to shift loading to the bone surrounding the nail device 20, and stress shielding for the femur 10 is substantially less as a result of the solid rod being converted to a plurality of segments.

In view of the aforegoing description, it is seen that a robust nail device in the form of an intramedullary rod can be implanted into a fractured bone to initially impart high strength characteristics to the fractured bone. As the bone heals, the bioresorbable adhesive is gradually absorbed into the fractured bone to reduce the high strength and stiffness characteristics of the nail device and gradually transmit loads to the healing bond. Over time the bioabsorbable adhesive will be fully absorbed so that the healing bone will be subjected to loads in order to provide for proper bone remodeling at the fracture site. Consequently, the gradual absorption of the bioresorbable adhesive will substantially parallel the gradual healing of the fractured bone.

What is claimed is:

1. A nail device for insertion into a fractured bone such that the nail device extends across a fracture site to provide stabilization while the bone is healing at the fracture site, the nail device including a plurality of segments cooperating with means for fastening the same together initially when the nail device is inserted into the bone so that the plurality of fastened segments impart bending strength to the fractured bone, the plurality of segments being disposed closely adjacent each other in parallel relation, the means for fastening comprising a bioresorbable adhesive which is responsive to its disposition within the fractured bone to gradually resorb and reduce the fastening of the plurality of segments such that over a period of time the plurality of segments are gradually disassociated to remain as discrete segments within the bone to permit a gradual increase in bending of the fractured bone as healing occurs.

2. The nail device of claim 1 in which the plurality of segments extend longitudinally from one end and the one end forms a solid construction.

3. The nail device of claim 2 in which the one end of the nail device includes means to position the nail device relative to the fractured bone as the nail device is inserted into the fractured bone.

4. The nail device of claim 2 in which the plurality of segments extend over a substantial length thereof.

5. The nail device of claim 2 in which the plurality of segments extend from an end comprising a solid member and the plurality of segments extend over about 80% of the length thereof.

6. The nail device of claim 2 in which the at least one end includes at least one opening to receive a screw for fixation of the one end to the fractured bone.

7. The nail device of claim 1 in which a spacing is defined between adjacent segments and a bioresorbable adhesive is disposed in the spacing.

8. A nail device having a plurality of segments extending longitudinally in spaced relation to each other and adhesive means disposed in the spacing to hold the plurality of segments together, the nail device being adapted for disposition relative to a fractured bone such that the adhesive is resorbed within the bone and the plurality of segments remain as discrete segments which impart less bending stiffness to the bone.

9. A nail device for implantation into a fractured bone to assist in the healing of the fractured bone, the nail device having a bending stiffness which changes from a first predetermined value to a second predetermined value in response to the time of implantation in the bone, and the nail device comprising a plurality of segments fastened together to form an individual rod defining the first predetermined value, and the plurality of segments are unfastened from each other over time to form individual segments defining the second predetermined value.

10. The nail device of claim 9 in which the first predetermined value of bending stiffness is greater than the second predetermined value of bending stiffness.

11. The nail device of claim 9 in which a plurality of segments are movably disposed adjacent each other to define the second predetermined value.

12. The nail device of claim 11 in which a resorbable adhesive material is used to hold the plurality of segments together.

* * * * *